United States Patent [19]

Epstein

[11] Patent Number: 5,826,546
[45] Date of Patent: Oct. 27, 1998

[54] METHOD FOR SHAMPOOING A PET USING A FOAM-DISPENSED PET SHAMPOO COMPOSITION

[75] Inventor: Kenneth R. Epstein, Dayton, Ohio

[73] Assignee: MiracleCorp of Australia, Dayton, Ohio

[21] Appl. No.: 839,146

[22] Filed: Apr. 23, 1997

[51] Int. Cl.$^6$ .......................... A01K 29/00; A61K 7/075
[52] U.S. Cl. ............................. 119/651; 132/202
[58] Field of Search .................. 119/601, 604, 119/651, 665, 671; 132/200, 202

[56] References Cited

U.S. PATENT DOCUMENTS

| | | | |
|---|---|---|---|
| 4,183,367 | 1/1980 | Goebel et al. | 132/202 |
| 4,820,308 | 4/1989 | Madrange et al. | 132/202 |
| 4,919,846 | 4/1990 | Nakama et al. | 510/433 |
| 4,933,371 | 6/1990 | Hink et al. | 514/739 |
| 5,009,197 | 4/1991 | Cottell | 119/651 |
| 5,070,819 | 12/1991 | Helmstetter | 119/604 |
| 5,215,748 | 6/1993 | Mankovitz | 424/195.1 |
| 5,271,530 | 12/1993 | Uehira et al. | 222/190 |
| 5,314,699 | 5/1994 | Baden | 424/660 |
| 5,337,929 | 8/1994 | van der Heijden | 222/402 |
| 5,346,639 | 9/1994 | Hatfield | 510/120 |
| 5,379,723 | 1/1995 | Branley | 119/601 |
| 5,385,733 | 1/1995 | Mankovitz | 424/195.1 |
| 5,443,569 | 8/1995 | Uehira et al. | 222/190 |
| 5,449,517 | 9/1995 | Fitzjarrell | 424/195.1 |
| 5,536,332 | 7/1996 | Chun | 132/202 |
| 5,632,231 | 5/1997 | Moore | 119/671 |

FOREIGN PATENT DOCUMENTS

| | | |
|---|---|---|
| 1027045 | 1/1974 | Canada . |
| 0734727 | 2/1996 | European Pat. Off. . |
| 2293547 | 3/1996 | United Kingdom . |
| 9110364 | 4/1991 | WIPO . |
| 9620267 | 12/1995 | WIPO . |
| 9628033 | 3/1996 | WIPO . |

Primary Examiner—Michael J. Carone
Assistant Examiner—Elizabeth Shaw
Attorney, Agent, or Firm—Thompson Hine & Flory LLP

[57] ABSTRACT

A method is described for shampooing a fur- or hair-bearing pet which comprises providing a waterless, foamable shampoo composition in a dispenser which includes a mixing chamber for mixing the shampoo composition with air, wherein foam is generated as the shampoo composition and air are released from the nozzle of the dispenser applying the waterless, foamable shampoo composition to the pet, rubbing the foam into the hair or fur of the pet, and drying the pet without the need for additional water to pre-wet the fur or hair for the pet or to rinse the pet after shampooing.

11 Claims, No Drawings

METHOD FOR SHAMPOOING A PET USING A FOAM-DISPENSED PET SHAMPOO COMPOSITION

BACKGROUND OF THE INVENTION

This invention relates to a method for shampooing a fur- or hair-bearing pet such as a dog or cat using a foamable composition in combination with a dispenser capable of dispensing the shampoo as a foam, without requiring the use of water to wet the fur or hair of the pet prior to or after bathing the pet.

Spray applicators particularly for shampoos are generally known and are disclosed, for example, in Neale et al., U.S. Pat. Nos. 3,701,475 and 3,752,399, and in Charitar et al. U.S. Pat. No. 5,116,253. While such spray applicators have been directed to the shampooing of human hair, the exploding population of house-hold pets has generated a demand for improved grooming methods aimed at the pet population.

Generally pet shampoos are sold as a liquid in a container such as a plastic bottle having a screw-on cap. When using shampoo to bathe a pet, one typically pre-wets the hair or fur of the pet and then simply pours an appropriate amount of the shampoo onto the pet and vigorously works the shampoo into a lather. It is generally known that pets such as dogs and cats and, particularly cats, have a strong dislike for being bathed. After the pet has been thoroughly bathed, the shampoo is revised from the hair or fur of the pet and the pet is dried using a towel. No matter how much toweling one does to dry the pet, a considerable amount of residual water remains in the hair or fur of the pet, and it is a natural instinct of the pet to try to remove the excess water by violently shaking its body and/or incessantly writhing about on the floor. This procedure for bathing a pet is an unpleasant experience, at best, and often can be traumatic for both the pet and the person bathing the pet. Shampoos which are dispensed as a liquid or a mist from a pump-actuated dispenser do not provide a solution to the problem because the need to pre-wet the hair or fur of the pet and to rinse the pet with water still exists. Therefore, it is desirable to provide a method for bathing a fur- or hair-bearing pet such as a cat or dog using a pet shampoo composition in combination with a shampoo dispenser from which the shampoo can be easily dispensed in a convenient form and which would allow the pet to be shampooed and dried without the need for additional water other than that in the shampoo composition.

SUMMARY OF THE INVENTION

In accordance with the present invention, a waterless method is provided for bathing a fur- or hair-bearing pet such as a dog or cat using a pet shampoo composition in combination with a dispenser which is capable of dispensing the shampoo composition as a foam. The composition comprises an appropriate combination of ingredients useful in a pet shampoo and may contain one or more of the following: anionic detergents, nonionic detergents, amphoteric detergents, preservatives, antimicrobial agents, antioxidants, mild soaps, surfactants, skin conditioners such as aloe extracts, fragrances, agents for treating flea infestation such as melaleuca oil, a pH adjuster such as citric acid, etc., depending on the particular need of the pet.

The care and grooming of pets often require a special shampoo composition which typically is effective for treating the skin of the animal as well as providing sheen and luster to the coat of the pet. While the composition of the pet shampoo may be important, the actual dispensing of the shampoo and the shampooing process is equally important.

Conventionally, foam dispensing containers rely upon a high pressure gas such as carbon dioxide or a fluorocarbon, e.g., Freon, to combine with a foamable liquid and dispense the liquid as a foam. The use of such foam dispensing containers are in public disfavor, however, because of the growing concern for the global environment.

The dispenser useful in applying the shampoo composition of the present invention is actuated by a manual pumping operation, wherein outer air is introduced, under pressure, into the liquid shampoo composition at a predetermined ratio in a mixing chamber. The mixing of the air and the liquid shampoo results in a foam which is homogenized and dispensed through the dispenser nozzle. Examples of such foam dispensers are described in U.S. Pat. Nos. 5,271,530 and 5,443,569, both to Uehira et al., the contents of which are incorporated herein by reference thereto for the purpose of describing foam dispensing pump containers useful in dispensing foam shampoo compositions in accordance with the present invention.

As used in this invention, the term "waterless", in defining the foamable shampoo composition means that the shampoo composition is used without the further addition of water either to pre-wet the hair or fur of the pet, or to rinse the shampoo from the hair or fur of the pet after shampooing.

The term "ingredients" as used herein means all components or agents other than water. Such ingredients may be essential or non-essential.

The present procedure calls for the shampoo composition to be applied to the hair or fur of the pet as a foam, followed by vigorously working the foamed composition into the hair or fur, and finally drying the pet, e.g., with a towel. No water is needed to either prewet the pet or to rinse the pet after it has been bathed.

DETAILED DESCRIPTION OF THE INVENTION

The present invention is a method for bathing a pet using a waterless, shampoo composition. Because the composition is a waterless shampoo, i.e., it is employed without the need for additional water other than that which is in the shampoo composition, the composition is particularly useful for bathing cats which typically display an intense aversion to being bathed.

In accordance with the invention, the shampoo formulation is dispensed from a foam-dispensing container which is characterized as a pump-actuated container which is provided with a mixing chamber for mixing the liquid shampoo component with air. The mixing chamber, typically, contains separate inlet ports for supplying the liquid shampoo component and the air to the mixing chamber in a predetermined ratio. Both the air and the shampoo composition are under pressure as a result of the actuation of the pump. The liquid shampoo component and the air are mixed in the mixing chamber to generate a foam. The foamed mixture, under pressure, is then dispensed through a dispensing nozzle connected to the mixing chamber outlet The shampoo composition useful in the present invention can be of any conventional formulation which is commonly used to bathe fur- or hair-bearing pets such as a dog or cat, and particularly a cat, provided that the composition does not contain an anti-foaming ingredient or any other ingredient in any substantial amount which would prevent foaming of the composition upon being dispensed.

Typical shampoo compositions found to be useful in bathing a fur- or hair-bearing pet such as a dog or cat are those containing one or more detergents, including anionic detergents, amphoteric detergents, nonionic detergents and mixtures thereof. Preferred anionic detergents include sulfonated and sulfated alkyl, aralkyl and alkaryl composition, alkyl succinates, alkyl sulfosuccinates and N-alkyl sarcosinates. Especially preferred are the ammonium and mono-, di- and tri-ethanol amine salts of alkyl and aralkyl sulfates, as well as the ammonium mono-, di- and tri-ethanolamine salts of alkyl and aralkyl sulfonates. Preferred anionic detergents include ammonium lauryl sulfosuccinate, ammonium lauryl sulfate, triethanolamine dodecylbenzene sulfonate, ammonium laureth sulfate and a mixture of alkylbenzene sulfonate/coconut oil based diethanolamide/ethoxylated concentrate. A combination of ammonium lauryl sulfate and ammonium laureth sulfate is particularly preferred in compositions where anionic detergents are employed because such combination provides quick and sustained lathering.

Suitable amphoteric detergents for pet shampoo compositions include the cocobetaines. Particular cocobetaines suitable for use as a pet shampoo are the cocamidoalkyl betaines. Especially preferred is cocamidopropyl betaine.

Suitable nonionic detergents for pet shampoo compositions include fatty acid alkanolamides and alkylene oxide (ethylene oxide and propylene oxide) condensates of hydrophobic bases such as a long-chain fatty acid or an alkyl phenol. Typical of the fatty acid alkanolamides are those having a total of 10 to 21 carbon atoms, such as lauric monoor diethanolamide, coconut oil mono- or diethanolamide, and lauric isopropanolamide. Commercially available nonionic detergents particularly suitable for as a pet shampoo include cocamide DEA and lauramide DEA available from Rhone-Poulenc, and a mixture of alkylbenzene sulfonate/coconut oil based diethanolamide/ethoxylated concentrate available from Witco corporation under the tradename Witcodet.

In addition to the detergent(s), other ingredients commonly employed in a pet shampoo composition include any or all of the following: preservatives, e.g., methylchloroisothiazolenone/methylisothiazolenone; mild soaps; surfactants; skin treating agents such as aloe extracts; melaleuca oil; pH adjuster, such as citric acid; pure fragrances; preservative/antimicrobial agents, such as methyl, ethyl, propyl and butyl esters of hydroxybenzoic acid components; hydrolyzed wheat germ; DM DM hydantoin; tocopheryl acetate; retinyl palmitate; propylene glycol; and botanical agents, such as a mixture of chrysanthemum extract, clove extract, comfrey extract, evening primrose extract, Hawaiian white ginger extract, honeysuckle extract, hyacinth extract, jasmine extract, jojoba extract, lavender extract, neutral henna extract, red rose extract, roman chamomile extract, rosemary extract, wheat germ extract, and wild cherry bark extract, available from Vege-Tech as Mela Blend.

While the amounts of ingredients are not particularly critical, a typical shampoo composition comprises about 2 to 10% or more ingredients in an aqueous based medium, preferably such composition contains about 90 to 98 % water and about 2 to 10% ingredients. The term ingredients as defined above is meant to define all components other than water. Preferably, the ingredients are present in an amount of about 1.0 to 5.0% detergent, about 0.01 to 1.0% melaleuca oil, about 0.01 to 1.0% pH adjuster, about 0.01 to 1.0% DM DM hydantoin, about 0.10 to 1.00% preservative/microbial or antioxidant and about 0.01 to 1.0% fragrance. In addition to these ingredients, other commonly used, non-essential ingredients can also be included in the shampoo composition.

For example, the following is representative of one pet shampoo composition for bathing a pet in accordance with the invention wherein the composition includes an aqueous medium which contains, in conventional amounts, a mixture of ammonium lauryl sulfate and ammonium laureth sulfate; cocamidopropyl betaine, cocamide DEA; fragrances, such as Mel-Fragrance D-5535 available from American Aromatics, Inc., hydrolyzed wheat protein; DM DM hydantoin; and methylchloroisothiazolinone/methylisothiazolenone; tocopheryl acetate; retinyl palmitate; and propylene glycol.

Another representative foamable shampoo composition for use in carrying out the present invention includes the following (by weight):

| INGREDIENT | PERCENT |
| --- | --- |
| Water | 95.39 |
| Witcodet[1] | 3.50 |
| Melaleuca oil | 0.05 |
| Mela Blend[2] | 0.01 |
| Citric Acid | 0.10 |
| Glydant[3] | 0.10 |
| Germaben II[4] | 0.75 |
| Mel Fragrance D-5535[5] | 0.10 |

[1] a nonionic detergent available from Witco Corporation
[2] a blend of botanical agents available from Vege-Tech.
[3] a preservative/antimicrobial available from Glyco, Inc.
[4] a preservative/antioxidant available from Sutton Laboratories.
[5] a fragrance available from American Aromatics, Inc.

While the above formulation is a typical pet shampoo useful in the present invention, neither the specified ingredients nor the amounts of the ingredients are intended to limit the shampoo composition with respect the invention described herein.

A particular advantage of the present invention is that a hair- or fur-bearing pet be easily and effectively shampooed and dried without the need for additional water during the course of shampooing and without the need for a water rinse.

Having described the invention in detail and by reference to the particular embodiments thereof, it will be apparent that numerous modifications and variations in both the shampoo composition and the dispenser are possible without departing from the scope of the invention as defined by the appended claims.

What is claimed is:

1. A method for shampooing a fur or hair-bearing pet, said method comprising:

providing a foamable shampoo composition in a dispenser, said dispenser including a mixing chamber for mixing said shampoo composition with air, thereby generating a foam;

dispensing said foam from said dispenser through a nozzle;

applying, said foam to the hair or fur of said pet;

rubbing said foam into the fur or hair of said pet; and drying said pet wherein said method is conducted without wetting the fur or hair of the pet with water other than the water in the foamable shampoo composition.

2. The method of claim 1 wherein said composition comprises an effective amount of a detergent selected from the group consisting of one or more anionic detergents, amphoteric detergents, non-ionic detergents, and mixtures thereof.

3. The method of claim 2 wherein said composition further comprises one or more ingredients selected from the group consisting of melaleuca oil, preservatives, fragrances, hydrolyzed wheat protein, tocopheryl acetate, retinyl palmitate, propylene glycol, citric acid, botanicals, antioxidants, and antimicrobials.

4. The method of claim 3 wherein said composition comprises about 2 to 10% ingredients with the balance being water.

5. The method of claim 1 wherein said pet is a cat.

6. The method of claim 1 wherein said foamable shampoo composition contains melaleuca oil.

7. The method of claim 1 wherein said composition is foamed in said dispenser by manually pumping air into said mixing chamber.

8. A method for shampooing a hair- or fur-bearing pet, said method comprising:

providing a foamable shampoo composition in a dispenser, said dispenser including a mixing chamber for mixing said shampoo composition with air, thereby generating a foam, said composition comprising about 90 to 98% water and about 2 to 10% ingredients, wherein said ingredients comprise a mixture of about 1.0 to 5.0% nonionic detergent, about 0.01 to 1.0% melaleuca oil, about 0.005 to 0.10% botanicals, about 0.01 to 1.0% citric acid, about 0.01 to 1.0% DM DM hydantoin, about 0.10 to 1.0% of a mixture of methyl and propyl esters of hydroxybenzoic acids and about 0.01 to 1.0% fragrance;

dispensing said foam from said dispenser through a nozzle;

applying said foam to the hair or fur of said pet;

rubbing said foam into the fur of said pet; and drying said pet wherein said method is conducted without wetting the fur hair of the pet with water other than the water in the foamable shampoo composition.

9. The method of claim 8 wherein said nonionic detergent is a mixture of alkylbenzene sulfonate/coconut oil based diethanolamide/ethoxylated concentrate.

10. The method of claim 8 wherein said pet is a cat.

11. The method of claim 6 wherein said composition is foamed in said dispenser by manually pumping air into said mixing chamber.

* * * * *